United States Patent
Holmberg (10) Patent No.: US 10,528,089 B2
(45) Date of Patent: Jan. 7, 2020

(54) ACOUSTIC MEANS FOR DETECTING IF THE CASING OF A COMMUNICATION DEVICE CONSTITUTES A CLOSED SPACE

(71) Applicant: ASCOM SWEDEN AB, Göteborg (SE)

(72) Inventor: Robert Holmberg, Göteborg (SE)

( * ) Notice: Subject to any disclaimer, the term of this patent is extended or adjusted under 35 U.S.C. 154(b) by 0 days.

(21) Appl. No.: 15/955,714

(22) Filed: Apr. 18, 2018

(65) Prior Publication Data

US 2018/0239397 A1  Aug. 23, 2018

Related U.S. Application Data

(63) Continuation of application No. PCT/SE2016/051009, filed on Oct. 18, 2016.

(30) Foreign Application Priority Data

Oct. 19, 2015 (SE) ........................................ 1551344

(51) Int. Cl.
*G06F 1/16* (2006.01)
*H04R 1/02* (2006.01)

(52) U.S. Cl.
CPC ........... *G06F 1/1677* (2013.01); *H04R 1/028* (2013.01)

(58) Field of Classification Search
CPC ..... G06F 1/1615; G06F 1/1677; G01N 29/11; G01N 29/12; G01N 29/14; G01N 29/44; G01M 3/24
USPC ...................................................... 455/575.1
See application file for complete search history.

(56) References Cited

U.S. PATENT DOCUMENTS

| | | | |
|---|---|---|---|
| 2005/0072236 A1* | 4/2005 | Heyman | G01N 29/07 73/602 |
| 2005/0153727 A1* | 7/2005 | Li | H04M 1/03 455/550.1 |
| 2008/0212815 A1* | 9/2008 | Jeong | H04R 25/402 381/313 |
| 2009/0164148 A1 | 6/2009 | Shinoda | |
| 2009/0167545 A1* | 7/2009 | Osaka | H04M 1/0274 340/647 |

FOREIGN PATENT DOCUMENTS

| | | |
|---|---|---|
| EP | 2 271 134 A1 | 1/2011 |
| GB | 2 428 476 A | 1/2007 |
| JP | 2009 121965 A | 6/2009 |
| JP | 2013 253836 A | 12/2013 |
| WO | WO-2011045879 A1 * 4/2011 | ............. G01B 17/00 |

* cited by examiner

*Primary Examiner* — Said M Elnoubi
(74) *Attorney, Agent, or Firm* — Gabriela B. Tomescu, Esq.; Bergenstråhle & Partners AB (57) ABSTRACT

Method and communication device adapted for detecting an opening in a casing a communication device, wherein the device comprises an acoustic speaker and an acoustic sensor. The acoustic speaker is arranged to distribute an acoustic signal within a casing of the communication device and the acoustic sensor is adapted to receive an acoustic signal response constituted of the acoustic signal and an echo of said acoustic signal. The communication device further being adapted to analyze the received acoustic signal response and determining if the casing constitutes a closed space.

15 Claims, 6 Drawing Sheets

ACOUSTIC MEANS FOR DETECTING IF THE CASING OF A COMMUNICATION DEVICE CONSTITUTES A CLOSED SPACE

This application is the continuation of International Application No. PCT/SE2016/051009, filed 18 Oct. 2016, which claims the benefit of Swedish Patent Application No. SE 1551344-3, filed 19 Oct. 2015, the entire contents of which are hereby incorporated by reference.

TECHNICAL FIELD

The present invention relates generally to acoustic detection means for a communication device.

BACKGROUND ART

For devices, especially in medical environment, it is essential to know the condition of the device and if any lids, covers, or similar are open. Communication devices used in medical environments generally comprises multiple lids that are opened and closed for different tasks. One example is when the device needs to be charged and the user thereby is required to connect the device to a power source, another is when a memory card, SIM card, or any other form of input media is entered into the device. The lids are important for water resistance properties and in order to eliminate the risk of sparks. For example, in some areas where gases are handled it is dangerous if a mobile device is not enclosed in a way preventing sparks from coming into contact with the environment outside the casing of the device. It is further essential for the function of the communication in such an environment that the communication devices still can safely be used.

In prior art it is known to arrange micro switches in order to indicate if for example a lid is open and to prevent the user from using a device that isn't properly assembled or configured. Preventing the user can be either through presenting warnings on a display or in some embodiments to disable the entire communication device. One way of ensuring this is for example to present the user with an alarm if a lid of the device is open. Ensuring that all lids are closed is important for many different reasons, for example in order to maintain water resistance and reduce the risk of contamination. It is further beneficial to ensure that all lids are closed in order to reduce the risk of the lids being damaged during normal use, especially if the device is a mobile device.

The prior art solutions have further drawbacks when for example ensuring that a device is water resistant. A mechanical switch is actuated by a small section of the lid and in reality only indicates that the particular section is closed. If the lid is damaged or broken it might not fulfill its purpose although the switch indicates that it is properly in place. There are no means for indicating if the lid is arranged in a faulty way and thereby may compromise the water resistance of the communication device even if the switch indicates that the lid is closed.

In prior art it is further known to arrange other types of sensors, such as acoustic or light sensors in order to detect if a lid is opened or closed. The acoustic solutions generally comprises a sensor and a speaker. The sensor is a microphone arranged at the lid or device opposite to the speaker and then evaluates if the device lid is opened or closed through measuring the volume of an acoustic signal. There are many drawbacks with this solution, especially in relation to the need of a sensor in the lid. Thereby, this solution has mostly been utilized for folding telephones wherein the lid for example is the keyboard or another solid structure already comprising electronic components.

SUMMARY OF INVENTION

An object of the present invention is to provide a solution that addresses at least some of the problems of the prior art through providing an acoustic detection means, such as an acoustic sensor, adapted to detect if the casing of a communication devices constitutes a closed space or not. For example such a solution could be used to detect if port lids of a device are open or properly closed.

Another object of the present invention is to provide a solution wherein a sensor or sensor arrangement can detect and provide indication for multiple openings in a communication device. Examples of such openings are charging ports, communication ports, and battery lids.

Yet another object of the present invention is to provide a solution wherein a faulty lid can be detected.

Another object of the present invention is to provide a solution wherein the status of multiple lids can be detected by means of the same sensor or sensor arrangement in order to reduce the number of components in a communication device.

Another object of the present invention is to provide a solution wherein existing components are utilized for additional functionality.

Thus the solution relates to a method for detecting an opening in a casing of a communication device. The communication device comprises an acoustic speaker and an acoustic sensor, and performs the steps:
  transmitting from the acoustic speaker an acoustic signal propagating inside the casing of the communication device,
  receiving to the acoustic sensor an acoustic signal response constituted of the acoustic signal and an echo of said acoustic signal,
  analyzing the received acoustic signal response, and
  determining if the casing constitutes a closed space.

In one embodiment the signal response is solely constituted of the echo of said acoustic signal.

In one embodiment the signal response is solely constituted of the acoustic signal.

It is one advantage with the present solution that an opening in a casing can be detected without any mechanical actuation or any moving parts. By limiting the number of moving parts the sensor becomes less sensitive to fatigue and external influences such as dirt and moisture. It is another advantage with the present solution that most communication devices, such as PDAs, mobile phones, smartphones, and tablets need an acoustic sensor and an acoustic speaker for other applications, such as telephone calls or similar communications. Thereby, can functionality be combined and the total number of components decreased.

It is yet another advantage with the present solution that one sensor can be utilized to detect if a casing is a closed space, if there is one opening, or if there are multiple openings/openings. It is furthermore an advantage that the signal response can be analyzed to detect if the opening is an opening supposed to exist in the communication device or if the opening is an indication of a damaged casing.

According to an embodiment the casing comprises an opening and said opening is adapted to be sealed with a cover means, and the following steps are performed:
  determining based on said acoustic signal response if said opening is sealed or opened.

According to an embodiment the opening is an opening adapted to host a port.

In one embodiment the opening is an opening adapted to be covered by a lid, cover, cap, coverlet, or panel and comprises a port, a connection, a battery or any other suitable means to be hidden behind a cover or lid.

It is one advantage that the present solution can detect if a lid, cover, cap, coverlet, panel, or any other form of opening in the casing of a device is open. In the same communication device many different openings can be arranged, for example openings adapted for a headset connector, charger, memory card, sim card, battery, and similar applications. The openings in water resistant device are often covered with a lid of some sort in order for the device to be water proof or water resistant when the lid is closed. The lids can furthermore serve other purposes such as preventing sparks from leaving the casing of the device.

According to an embodiment the opening is a charging port adapted to be closed with the cover means.

According to an embodiment of the present solution the acoustic speaker and acoustic sensor as described herein can be utilized for detecting if a communication device no longer is water proof, water resistant, or spark proof.

It is one advantage with the present solution that through analyzing the signal response it is possible to detect if a charging port is opened or closed. In communication devices a charging port is used for charging the device when it is not used or it is required for the devices to be charged since the battery is drained. The lid of the charging port is thereby opened and closed a vast number of times during the life time of the device. Although the lid is operated often it is very important to make sure that the lid is properly closed every time.

In one embodiment the communication device is water proof, water resistant, or spark proof if a connector is inserted to a port hosted in the opening of the casing. The solution can detect if the casing constitutes a closed space or not and thereby it is one advantage that different cover means can be arranged in the opening and the sensor arrangement will still acknowledge their existence and also verify their functionality through ensuring that the casing constitutes a closed space. For example, a connector or a lid could potentially at different points in time cover the same opening 5.

According to an embodiment the casing comprises multiple openings and the solution further comprises:

determining based on said acoustic signal response which out of the multiple openings of the casing that are open or sealed.

It is yet another advantage with the present solution that in addition to detecting if one or more openings of the casing of a device are opened or closed it is possible through signal analysis of the acoustic signal to determine which of many lids that are open. For example, the system can indicate if one, two, or more lids are open and if for example the battery lid and the charging port lid are open but the headphone lid is closed.

According to an embodiment the acoustic response is received by multiple acoustic sensors.

According to an embodiment multiple sensors are utilized to receive the signal response in order to improve the accuracy of the system.

In one embodiment two acoustic sensors are arranged with a distance between the sensors enabling that a form of stereo sound can be picked up. The stereo sound which is for each channel a representation of the signal response can be analyzed and the accuracy of the system can thereby be improved.

According to an embodiment the acoustic signal is transmitted from multiple acoustic speakers.

In one embodiment similar advantages can be reached by instead of arranging multiple acoustic sensors arranging multiple acoustic speakers.

According to an embodiment multiple speakers are used to transmit the acoustic signal in order to generate a signal response with more information to analyze.

According to an embodiment both multiple acoustic speakers and multiple acoustic sensors are used to determine if one or more lids, covers, or ports are opened and/or if the casing constitutes a closed space.

According to an embodiment the solution further comprises:

analyzing the signal response to determine if the communication device is in contact with a person.

It is another advantage with the present solution that it is possible to determine if a communication device is for example held by a person, located in a pocket, or if it is resting on a table. This is achieved through analyzing the acoustic signal response and especially the characteristics of how the echo of the acoustic signal is reflected by the casing. This is beneficial in order to determine the status of the device, if it is in use, and what it is used for.

It is yet another advantage that through detecting if a devices is held by a person, placed in a pocket, or how it is stored it is possible via an algorithm to establish if the communication device is currently used by an individual user. This is important in order to for example establish that the devices is located in such a way that the user will attend to information sent to the device.

In one embodiment can other means such as positioning means, means for detecting movement, or any other form of suitable means be used in combination with the solution as presented herein in order to determine if a devices is used by a person or not. Additionally can a timer or similar be used to measure inactivity.

In another embodiment the same solution can be used for a wall mounted communication device, such as an access point, in order to determine if the communication device still is properly arranged to the wall or not.

According to an aspect of a communication device comprising an acoustic speaker and an acoustic sensor the acoustic speaker is arranged to distribute an acoustic signal within a casing of the communication device. The acoustic sensor is adapted to receive an acoustic signal response constituted of the acoustic signal and an echo of said acoustic signal, the communication device further being adapted to analyze the received acoustic signal response and determining if the casing constitutes a closed space.

According to an embodiment of the communication device the casing comprises an opening, said opening is adapted to be sealed with a cover means, and the communication device is adapted to determine based on said acoustic signal response if said opening is sealed or opened.

According to an embodiment the communication device is adapted to analyze the acoustic signal response to determine if a connector is attached to a port arranged in the opening.

According to an embodiment of the communication device the opening is adapted to host a cover means.

According to an embodiment of the communication device the cover means is any one of a battery lid, a charging port lid, or a memory card slot lid. The person skilled in the art understands that the cover means further can be any form of cover means suitable for the communication device application.

According to an embodiment of the communication device the casing comprises multiple openings and the communication device further is adapted to determining which out of multiple openings that are open or closed based on said signal response.

According to an embodiment of the communication device the acoustic signal is transmitted by multiple acoustic speakers and/or the signal response is received by multiple acoustic sensors.

According to an embodiment the communication device is further adapted to analyze the signal response to determine if the communication device is in contact with a person.

According to an embodiment the communication device further comprises a memory and a central processing unit. The central processing unit (CPU), or any other unit of the communication device adapted for computations, is configured to analyze the signal response with the known acoustic signal in memory. The CPU is further adapted based on said analysis to determine if the casing constitutes a closed space or not.

According to an embodiment is the communication device a mobile communication device. For the purpose of this disclosure a mobile communication device is a device adapted for communication and that can be carried by a user, such as a PDA, smartphone, mobile phone, tablet, or any other form of device that can be used for communication and carried around.

According to an embodiment when a communication device has indicated for more than a certain threshold, for example a week, that the casing of the communication device no longer constitutes a closed space, the communication device indicates that it is time for service of the device. In one embodiment is the communication device automatically placed in a service mode requiring action before the device can be used again.

BRIEF DESCRIPTION OF DRAWINGS

The invention is now described, by way of example, with reference to the accompanying drawings, in which.

DESCRIPTION OF EMBODIMENTS

In the following, a detailed description of the different embodiments of the invention is disclosed under reference to the accompanying drawings. All examples herein should be seen as part of the general description and are therefore possible to combine in any way of general terms. Individual features of the various embodiments and aspects may be combined or exchanged unless such combination or exchange is clearly contradictory to the overall function of the solution and system.

Briefly, the solution relates to acoustic means for detecting if a casing of a communication device constitutes a closed space or if there are any openings, holes, broken sections, or apertures in the casing. The solution could be implemented in any form of communication device, such as a smartphone, PDA, tablet, access point, or any other form of devices. The communication device can for example be a mobile communication device and in one embodiment be handheld, however in other embodiments could the communication device be arranged in any other way, such as mounted on a wall.

Figure 1:
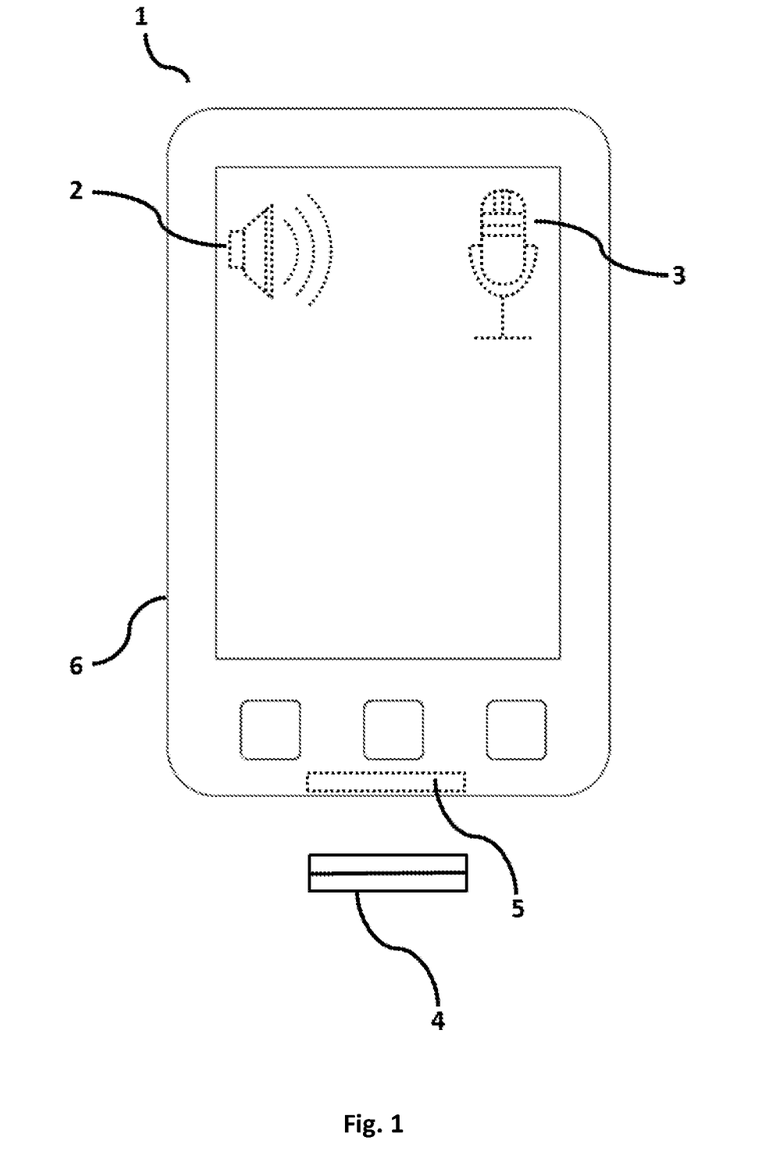
FIG. 1 illustrates an embodiment of the communication device comprising an acoustic speaker and an acoustic sensor.

FIG. 1 illustrates a communication device 1 comprising an acoustic speaker 2 and an acoustic sensor 3. The communication device 1 can in different embodiments be different sorts of devices 1, including but not limited to a mobile phone, a smartphone, a PDA, a tablet, a general purpose computer, an access point, or any other form of communication device 1. The acoustic speaker 2 is a speaker adapted to distribute a sound signal. In one embodiment is the sound distributed in a frequency range that can be perceived by humans, in another is the acoustic speaker 2 adapted to distribute a sound outside of the frequency range that a human can perceive. In yet another embodiment is the acoustic speaker 2 adapted to distribute sound both in a frequency spectra that can be perceived by a human and in a spectra that can't.

The communication device 1 further comprises a casing 6 which encompass the components of the communication device 1. In one embodiment the casing 6 further comprises at least one opening 5 that is adapted to receive some form of input or allow access to some of the components of the communication device 1. Examples are a charging port or a battery lid. The communication device 1 is adapted to not have any open openings during normal use and therefore further comprises lids 4, covers 4, or other means 4 adapted to seal or close the openings of the communication device 1 when the opening 5 is not required, for example is the charging port not required when the user moves around and are using the communication device 1 with a battery as the power source. The lids 4, covers 4, or other means adapted to seal or close the openings 5 are herein collectively called cover means 4 and are adapted to close or seal the openings 5.

As known to the person skilled in the art the communication device 1 may further comprise other components, including but not limited to a memory, a CPU, and other means required or useful for such a device 1.

Figure 2:
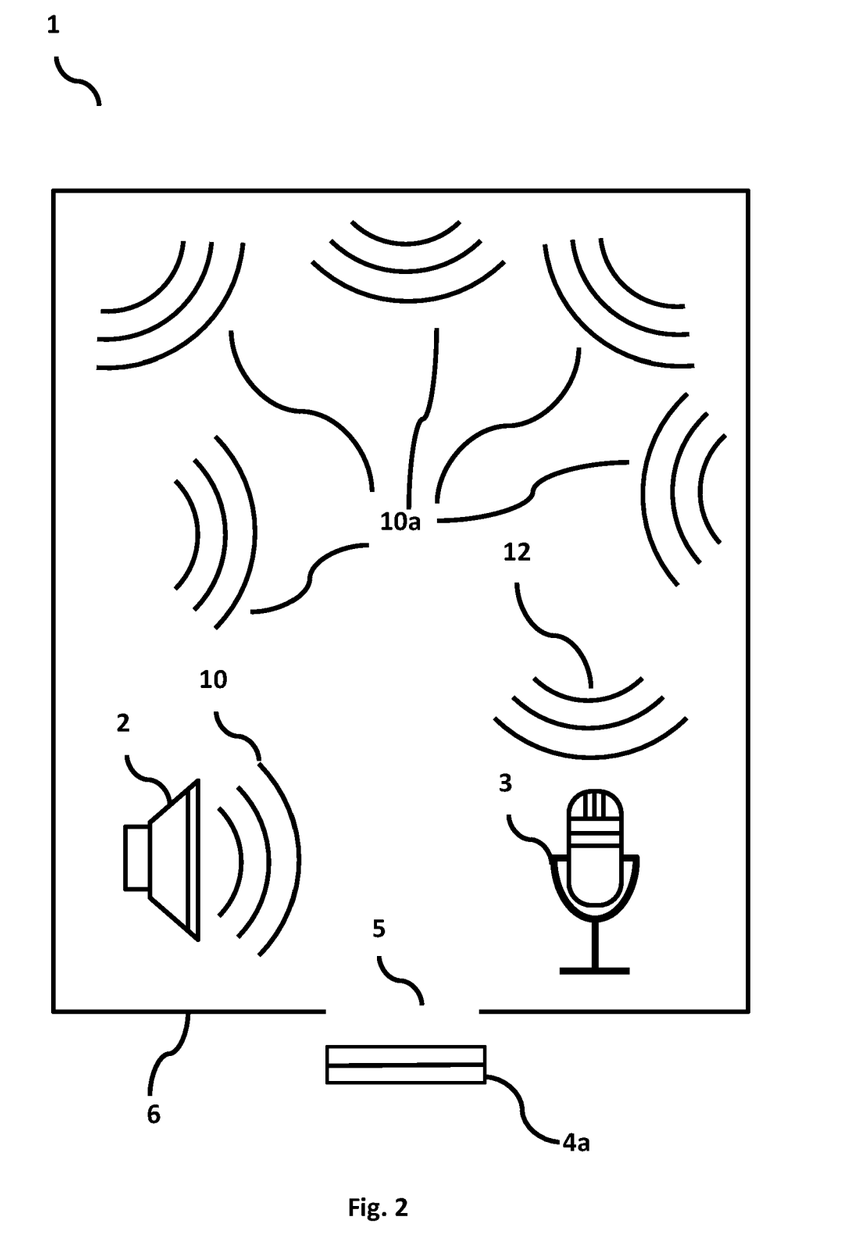
FIG. 2 shows an illustrative view of one embodiment of a communication device comprising an acoustic speaker and an acoustic sensor wherein the acoustic echo and acoustic response signal are illustrated.

FIG. 2 shows an illustrative view of the communication device 1 comprising an acoustic speaker 2 and an acoustic sensor 3, wherein the acoustic sensor 3 and acoustic speaker 2 are active.

One example of a communication device 1 comprises a single opening 5 as illustrated in FIG. 2. The opening 5 can be sealed or closed with a cover 5, if it is sealed or closed depends on if the device 1 is designed to be water proof, water resistant, or spark proof or if the device 1 is designed for a purpose without any one of those requirements. The exact design of the cover, lid, or in more general terms the cover means 4 is not of particular interest to the solution and the acoustic sensor 3 and acoustic speaker 2 are not dependent of the cover means 4 and thus arranged to detect any opening 5 in the casing 6. The acoustic speaker 2 is adapted to transmit an acoustic signal 10 that spread inside the communication device 1. The propagating sound hits the different surfaces of the casing 6 and creates an echo 10a of the acoustic signal 10. The acoustic signal 10 and the echo 10a together constitutes a signal response 12 that is detected by the acoustic sensor 3. The signal response 12 is analyzed and it is determined if the opening 4 is closed or open.

Depending on how the signal is defined and for how long the signal is transmitted the signal response 12 is constituted of the echo 10a together with the acoustic signal 10 or only the echo 10a. In one embodiment is the signal response 12 initially constituted of only the acoustic signal 10, than the acoustic signal 10 and the echo 10a, and just before the end of the signal it is only constituted of the echo 10a.

Figure 3:
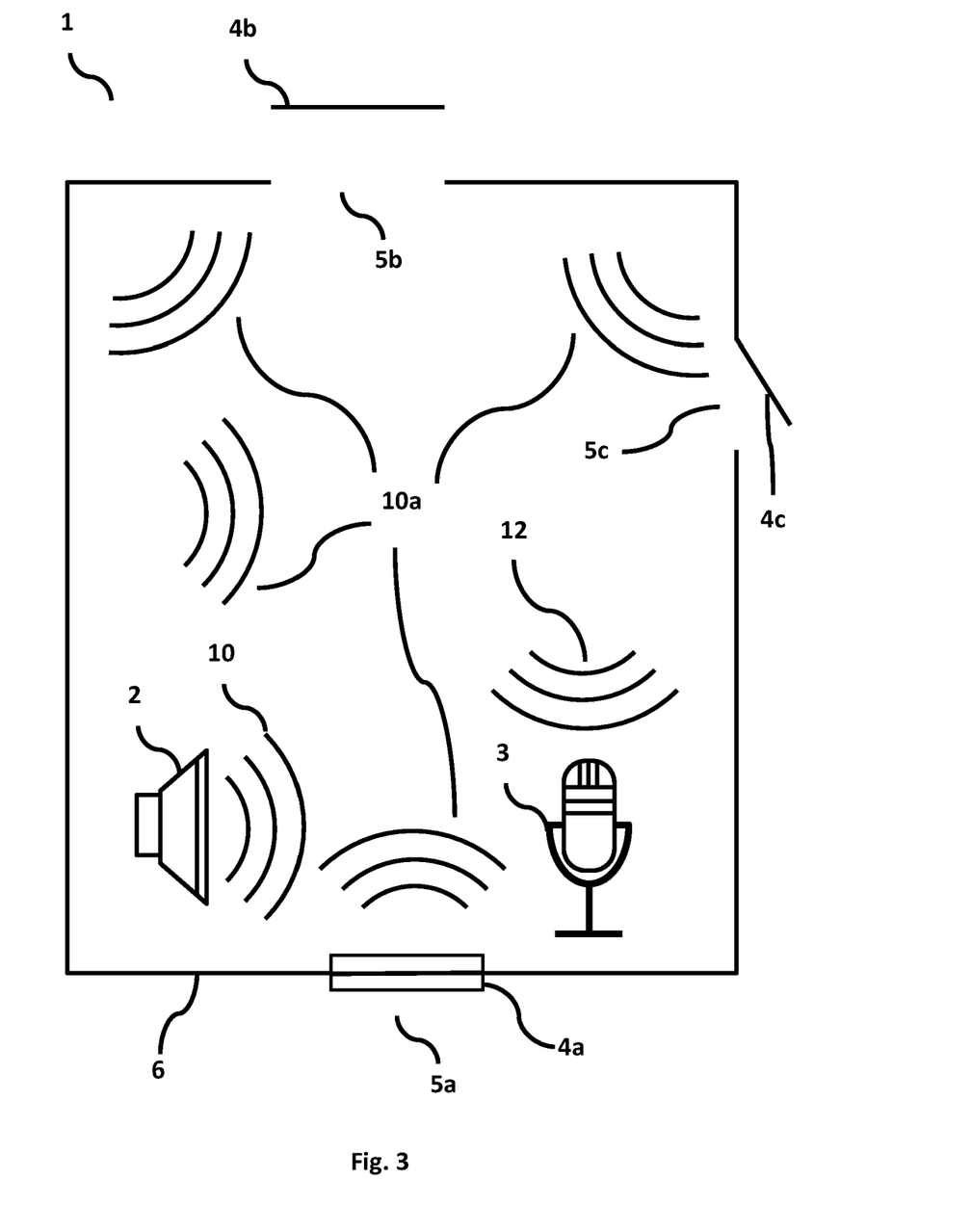
FIG. 3 illustrates another embodiment of a communication device wherein the casing of the device comprises multiple openings.

FIG. 3 shows another embodiment of the communication device 1 similar to the illustrative view as shown in FIG. 2. For the purpose of example the casing 6 of the communication device 1 as illustrated in FIG. 3 comprises multiple openings 5a, 5b, 5c arranged at different sides of the communication device 1 casing 6. The opening 5a is recognized from the embodiment as illustrated in FIG. 2 but is here closed or sealed with the cover means 4. The remaining openings 5b, 5c also have corresponding cover means 4b, 4c that are not closed in the example as illustrated in FIG. 3. As can be seen from the difference between FIGS. 2 and 3 the eco 10a is different depending of which one of the openings 5a, 5b, 5c that are open. Thereby also the signal response 12 becomes different and the signal response 12 can be analyzed to indicate which of the openings 5a, 5b, 5c that are open.

FIG. 3 further illustrates how different openings 5a, 5b, 5c can be used for different purposes. For example, the first opening 5a could be a charging port with a cover 4a, the second opening 5b could be a battery access opening with a battery lid 4b, and the third opening 5c could be a communication port with a cover 4c.

The examples as shown by FIGS. 2 and 3 are merely examples and the number of openings 5 are not limiting to the scope of the solution.

In one embodiment the solution as described herein can be explained in a simplified way with the example of a musical flute. The solution utilizes the same physic phenomenon for the cover means 4 as the flute utilize when the person playing the flute covers one or more holes in the flute with one or more fingers.

Figure 4A:
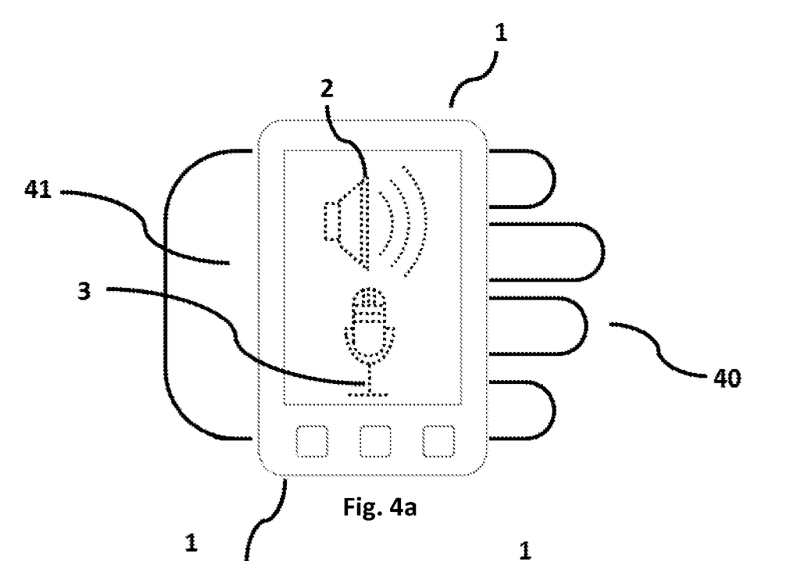
FIG. 4a illustrates a communication device held in the palm of a user.

FIG. 4a illustrates a communication device 1, such as a mobile communication device 1, held in the palm 41 of a user's hand 40. The acoustic sensor 2 transmits an acoustic signal 10 within the communication device 1. The acoustic signal 10 hits the internal perimeters of the casing 6 and echoes back as an echo 10a that is received by the acoustic sensor 3. The signal response 12 received by the acoustic sensor 3 is analyzed to determine how the echo 10a was affected by the perimeters of the casing 6. Based on the echo 10a in the signal response 12 it is thereby possible to determine if the communication device 1 for example is held in the palm 41 of a hand 40. The same solution can in other embodiments be utilized to determine if the communication device 1 is located in a pocket, on a table, or any other form of location wherein the casing 6 is in contact with another surface.

Figure 4B:
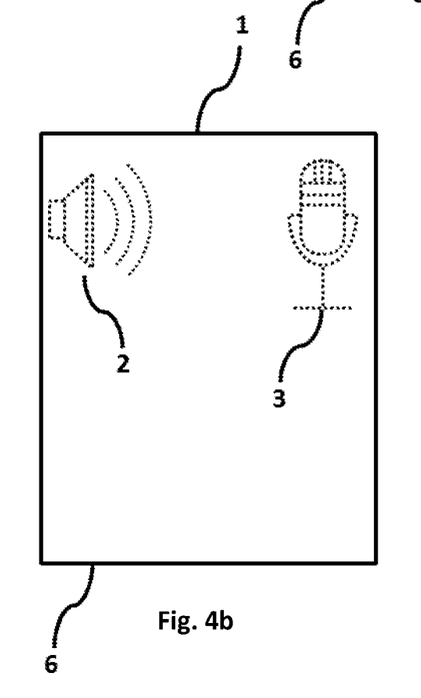
FIG. 4b illustrates a communication device wherein the casing constitutes a closed space.

FIG. 4b illustrates an embodiment of the communication device 1 wherein the casing 6 constitutes a closed space. A closed space is for the purpose of this disclosure a space being substantially closed or sealed.

Figure 4C:
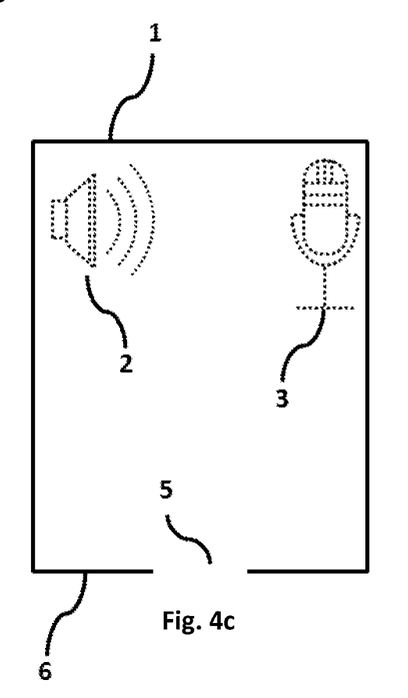
FIG. 4c illustrates a communication device wherein the casing comprises an open opening.

FIG. 4c illustrates an embodiment of the communication device 1 wherein the casing 6 do not constitute a closed space. The opening 5 in the casing compromises the closed space of the casing 6 and thereby the casing 6 do not constitutes a closed space in the example of FIG. 4c.

Figure 5:
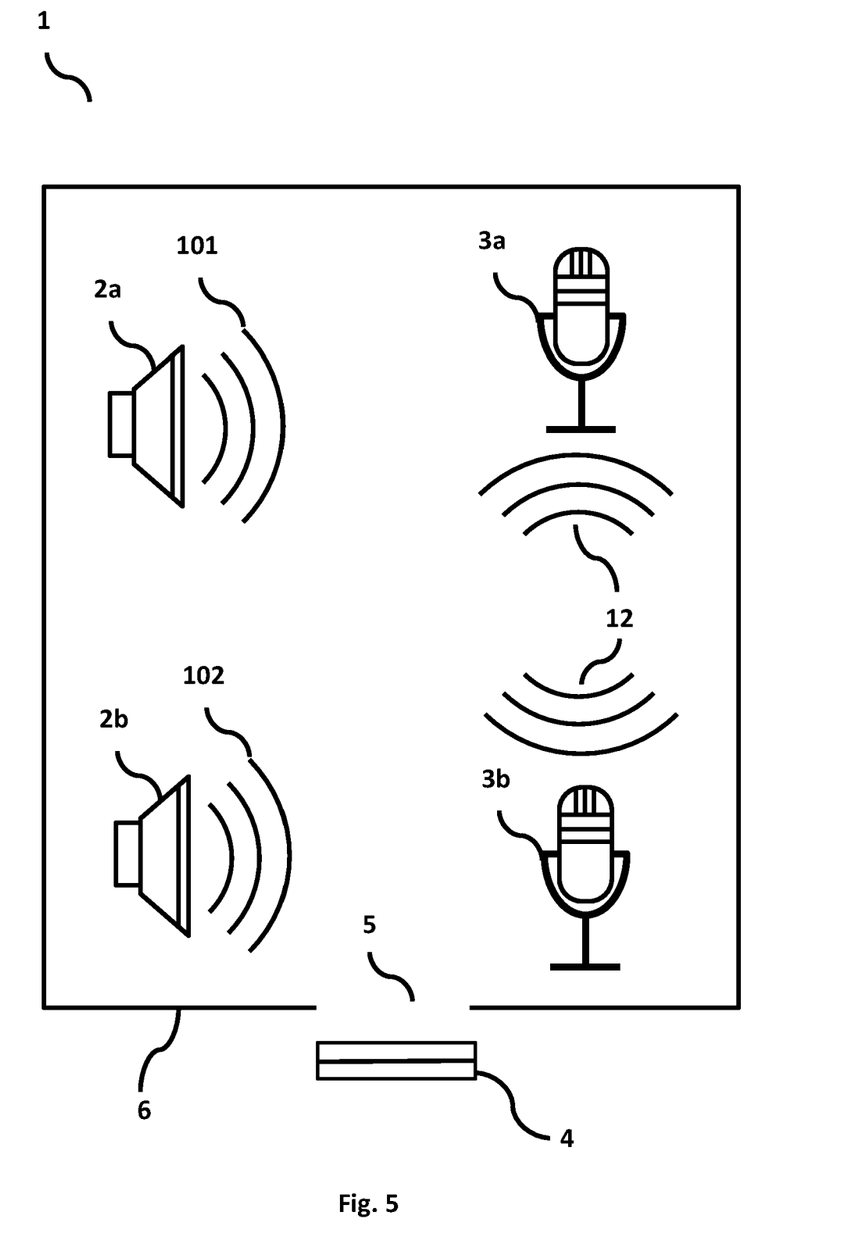
FIG. 5 illustrates a communication device comprising two acoustic speakers, two acoustic sensors, and an opening.

FIG. 5 illustrates an embodiment of the communication device 1 wherein multiple acoustic speakers 2a, 2b and acoustic sensor 3a, 3b are arranged. Arranging multiple acoustic sensors 3a, 3b and/or multiple acoustic speakers 2a, 2b in some embodiments significantly increases the accuracy for detecting if the casing 6 constitutes a closed space or not. For example, in one embodiment multiple acoustic speakers 2a, 2b transmits two acoustic signals 101, 102 wherein the acoustic signals 2a, 2b are identical to one another. The acoustic signals 101, 102 are transmitted from different locations within the casing 6 and received by an acoustic sensor 3a. In another embodiment the same solution is used but with multiple acoustic sensors 3a, 3b. Through sending the acoustic signals 101, 102 from different locations within the casing 6 the echoes from each of the acoustic signals 101, 102 are reflected with different characteristics by the casing 6 increasing the amount of information to analyze in order to determine if the casing 6 constitutes a closed space or not.

In another embodiment are two acoustic signals 101, 102 transmitted from two different acoustic speakers 2a, 2b wherein the acoustic signals 101, 102 are transmitted with an offset in time. The acoustic signals 101, 102 could in one embodiment be identical signals transmitted with an offset and in another different signals transmitted with an offset. The signal response is dependent of the purpose for the specific embodiment received by either one or multiple acoustic sensors 3a, 3b. Through arranging multiple acoustic sensors 3a, 3b it is possible to record the signal response 12 at different locations within the casing 6 and thereby further improve the accuracy of the solution.

Figure 6:
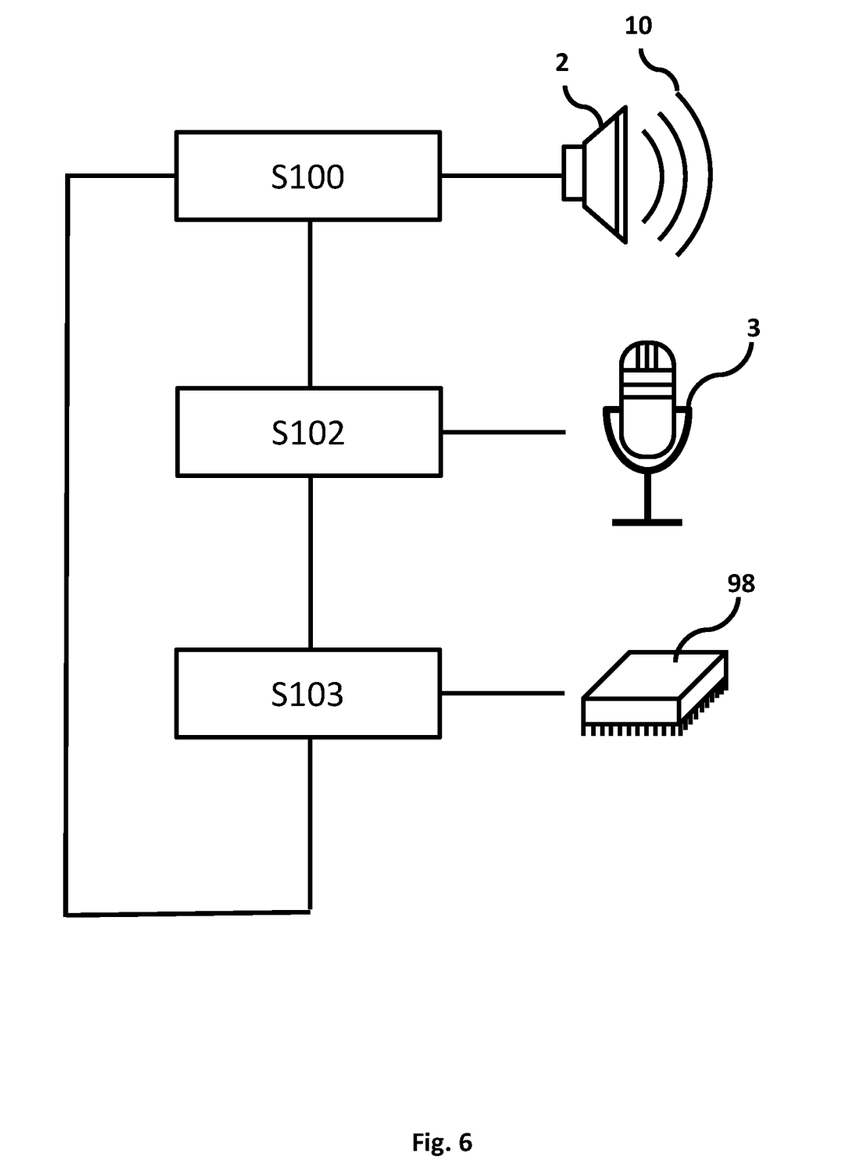
FIG. 6 shows a flow chart comprising an illustrative view of the solution.

FIG. 6 shows a flow chart illustrating steps performed in a communication device 1 in order to determine if the casing 6 constitutes a closed space or not. The acoustic speaker 2 transmits an acoustic signal 10 inside the casing 6 of the communication device 1. The acoustic signal 10 propagate inside the casing 6 and an echo 10a occurs inside the communication device 1. An acoustic sensor 3 receives S102 the transmitted echo 10a and/or the acoustic signal 10 and a processor analyzes S103 the received signal response.

As used herein the term acoustic refers to an audio sound, ultra-sonic sound, resonance, vibration, or any other form of acoustic signal that can be received by an acoustic sensor. The term "and/or" comprises any and all combinations of one or more of the associated listed items.

The invention claimed is:

1. A method for detecting an opening in a casing of a communication device, wherein the communication device comprises an acoustic speaker and an acoustic sensor, wherein the method comprises:

transmitting from the acoustic speaker an acoustic signal propagating inside the casing of the communication device, receiving to the acoustic sensor an acoustic signal response, analyzing the received acoustic signal response, determining, based on said received acoustic signal response, if the casing has one or more openings, determining if such openings are supposed to exist in the casing of the communication device or if the opening is an indication of a damaged casing.

2. The method according to claim 1, wherein the casing comprises an opening and said opening is adapted to be closed with a cover means, wherein the method further comprises:
   determining, based on said acoustic signal response, if said opening is closed, sealed, or opened.

3. The method according to claim 1, wherein said signal response is constituted of the acoustic signal and an echo of said acoustic signal.

4. The method according to claim 1, wherein the casing comprises multiple openings and the method further comprises
   determining, based on said acoustic signal response, which out of the multiple openings of the casing that are open, closed, or sealed.

5. The method according to claim 1, wherein the acoustic response is received by multiple acoustic sensors.

6. The method according to claim 1, wherein the acoustic signal is transmitted from multiple acoustic speakers.

7. The method according to claim 1, wherein the method further comprises:
   analyzing the signal response to determine if the communication device is in contact with a person.

8. A communication device comprising an acoustic speaker and an acoustic sensor, wherein the acoustic speaker is arranged to distribute an acoustic signal within a casing of the communication device, the acoustic sensor is adapted to receive an acoustic signal response constituted of the acoustic signal and an echo of said acoustic signal, the communication device further being adapted to analyze the received acoustic signal response and determining, based on said received acoustic signal response, if the casing has one or more openings and if the one or more openings are supposed to exist in the casing or if the casing is damaged.

9. The communication device according to claim 8, wherein the casing comprises an opening, said opening is adapted to be closed with a cover means, and the communication device is adapted to determine, based on said acoustic signal response, if said opening is sealed, closed, or opened.

10. The communication device according to claim 9, wherein the communication device is adapted to analyze the acoustic signal response to determine if a connector is attached to a port arranged in the opening.

11. The communication device according to claim 9, wherein the opening is adapted to host a cover means.

12. The communication device according to claim 11, wherein the cover means is any one of a battery lid, a charging port lid, or a memory card slot lid.

13. The communication device according to claim 9, wherein the casing comprises multiple openings and the communication device further is adapted to determining which out of multiple openings that are open or closed based on said signal response.

14. The communication device according to claim 9, wherein the acoustic signal is transmitted by multiple acoustic speakers and/or the signal response is received by multiple acoustic sensors.

15. The communication device according to claim 9, wherein the communication device further is adapted to analyze the signal response to determine if the communication device is in contact with a person.

* * * * *